(12) United States Patent
Hillukka et al.

(10) Patent No.: US 8,893,370 B2
(45) Date of Patent: Nov. 25, 2014

(54) SYSTEM FOR LOADING A COLLAPSIBLE HEART VALVE

(75) Inventors: Brett Allen Hillukka, Hanover, MN (US); Khoi Le, Excelsior, MN (US); Ralph Joseph Thomas, Champlin, MN (US); Valerie J. Glazier, Eden Prairie, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 253 days.

(21) Appl. No.: 13/535,591

(22) Filed: Jun. 28, 2012

(65) Prior Publication Data

US 2013/0166020 A1 Jun. 27, 2013

Related U.S. Application Data

(60) Provisional application No. 61/512,637, filed on Jul. 28, 2011.

(51) Int. Cl.
| | | |
|---|---|---|
| *B21D 39/00* | (2006.01) | |
| *A61F 2/24* | (2006.01) | |
| *A61F 2/00* | (2006.01) | |
| *A61F 2/95* | (2013.01) | |

(52) U.S. Cl.
CPC ....... *A61F 2/2427* (2013.01); *A61F 2250/0064* (2013.01); *A61F 2250/0007* (2013.01); *A61F 2250/0039* (2013.01); *A61F 2/0095* (2013.01); *A61F 2002/9522* (2013.01); *A61F 2/2412* (2013.01)
USPC .......................................... 29/505; 623/2.11

(58) Field of Classification Search
CPC .... B21D 30/048; B21D 39/20; B21D 39/206; A61F 2/2427; A61F 2/0095; A61F 2/2412; A61F 2250/0064; A61F 2250/0007; A61F 2250/0039; A61F 2002/9522
USPC .......... 29/505, 506, 508, 428; 623/2.11, 1.11, 623/909
See application file for complete search history.

(56) References Cited

U.S. PATENT DOCUMENTS

| | | |
|---|---|---|
| 3,657,744 A | 4/1972 | Ersek |
| 4,423,730 A | 1/1984 | Gabbay |

(Continued)

FOREIGN PATENT DOCUMENTS

| | | |
|---|---|---|
| EP | 1129744 A1 | 9/2001 |
| EP | 1157673 A2 | 11/2001 |

(Continued)

OTHER PUBLICATIONS

International Search Report for Application No. PCT/US2011/001598 dated Jul. 6, 2012.

(Continued)

*Primary Examiner* — John C Hong
(74) *Attorney, Agent, or Firm* — Lerner, David, Littenberg, Krumholz & Mentlik, LLP

(57) ABSTRACT

An assembly for collapsing a self-expanding prosthetic heart valve includes a compression member, a support member, a constricting member, and a spacer which may be used for smaller sized heart valves. The compression member has a tapered wall between its first open end and its second open end, the tapered wall defining an open space adapted to receive the heart valve. The support member has a base and a recess adapted to receive an end of the heart valve. The support member and the compression member are movable toward one another to compress the heart valve and push it through a relatively small aperture in the second open end of the compression member. The second end of the constricting member is sized to receive the compressed heart valve from the second open end of the compression member for loading into a delivery device.

15 Claims, 13 Drawing Sheets

(56) References Cited

U.S. PATENT DOCUMENTS

| | | |
|---|---|---|
| 5,843,167 A | 12/1998 | Dwyer et al. |
| 5,924,424 A | 7/1999 | Stevens et al. |
| 5,968,068 A | 10/1999 | Dehdashtian et al. |
| 6,077,297 A | 6/2000 | Robinson et al. |
| 6,132,458 A | 10/2000 | Staehle et al. |
| 6,306,141 B1 | 10/2001 | Jervis |
| 6,471,718 B1 | 10/2002 | Staehle et al. |
| 6,623,518 B2 | 9/2003 | Thompson et al. |
| 6,814,746 B2 | 11/2004 | Thompson et al. |
| 6,830,584 B1 | 12/2004 | Seguin |
| 6,935,389 B1 | 8/2005 | Rinaldi |
| 7,014,074 B1 | 3/2006 | Rinaldi |
| 7,018,406 B2 | 3/2006 | Seguin et al. |
| 7,311,730 B2 | 12/2007 | Gabbay |
| 7,510,572 B2 | 3/2009 | Gabbay |
| 7,682,390 B2 | 3/2010 | Seguin |
| 7,803,185 B2 | 9/2010 | Gabbay |
| 8,561,967 B2 | 10/2013 | Hendriksen et al. |
| 8,585,019 B2 | 11/2013 | Melsheimer et al. |
| 2003/0050694 A1 | 3/2003 | Yang et al. |
| 2003/0070682 A1 | 4/2003 | Wilson et al. |
| 2004/0210304 A1 | 10/2004 | Seguin et al. |
| 2005/0137695 A1 | 6/2005 | Salahieh et al. |
| 2005/0137697 A1 | 6/2005 | Salahieh et al. |
| 2006/0074484 A1 | 4/2006 | Huber |
| 2006/0106415 A1 | 5/2006 | Gabbay |
| 2006/0142848 A1 | 6/2006 | Gabbay |
| 2006/0167468 A1 | 7/2006 | Gabbay |
| 2006/0259120 A1 | 11/2006 | Vongphakdy et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0073391 A1 | 3/2007 | Bourang et al. |
| 2007/0088431 A1 | 4/2007 | Bourang et al. |
| 2007/0112422 A1 | 5/2007 | Dehdashtian |
| 2007/0162100 A1 | 7/2007 | Gabbay |
| 2007/0168013 A1 | 7/2007 | Douglas |
| 2007/0203575 A1 | 8/2007 | Forster et al. |
| 2007/0239271 A1 | 10/2007 | Nguyen |
| 2007/0244552 A1 | 10/2007 | Salahieh et al. |
| 2007/0270931 A1 | 11/2007 | Leanna et al. |
| 2007/0270932 A1 | 11/2007 | Headley et al. |
| 2008/0071369 A1 | 3/2008 | Tuval et al. |
| 2008/0147182 A1 | 6/2008 | Righini et al. |
| 2008/0221703 A1 | 9/2008 | Que et al. |
| 2009/0054975 A1 | 2/2009 | del Nido et al. |
| 2009/0093876 A1 | 4/2009 | Nitzan et al. |
| 2009/0143857 A1 | 6/2009 | Melsheimer et al. |
| 2010/0004740 A1 | 1/2010 | Seguin et al. |
| 2010/0051886 A1 | 3/2010 | Cooke et al. |
| 2010/0286768 A1 | 11/2010 | Alkhatib |
| 2010/0298931 A1 | 11/2010 | Quadri et al. |
| 2011/0224678 A1 | 9/2011 | Gabbay |
| 2012/0078352 A1 | 3/2012 | Wang et al. |
| 2012/0330408 A1 | 12/2012 | Hillukka et al. |
| 2013/0190859 A1* | 7/2013 | Hillukka ............... 623/2.11 |

FOREIGN PATENT DOCUMENTS

| | | |
|---|---|---|
| WO | 2007071436 A2 | 6/2007 |
| WO | 2007081940 A2 | 7/2007 |
| WO | 2008070797 A2 | 6/2008 |
| WO | 2009/091509 A1 | 7/2009 |
| WO | 2010014834 A1 | 2/2010 |
| WO | 2010051025 A1 | 5/2010 |
| WO | 2010087975 A1 | 8/2010 |
| WO | 2010096176 A1 | 8/2010 |
| WO | 2012023979 A2 | 2/2012 |
| WO | 2012036742 A2 | 3/2012 |
| WO | 2012036744 A2 | 3/2012 |
| WO | 2012057983 A1 | 5/2012 |
| WO | 2012106491 A1 | 8/2012 |

OTHER PUBLICATIONS

Overview of PRE-CE Mark Transcatheter Aortic Valve Technologies (powerpoint—dated Jun. 1, 2010).

International Search Report and Written Opinion for Application No. PCT/US2012/023576 dated Jul. 6, 2012.

International Search Report for Application No. PCT/US2012/048298 dated Nov. 7, 2012.

International Search Report for Application No. PCT/US2012/048307 dated Feb. 28, 2013.

Quaden et al., "Percutaneous aortic valve replacement: resection before implantation", pp. 836-840, European J. of Cardio-thoracic Surgery, 27 (2005).

* cited by examiner

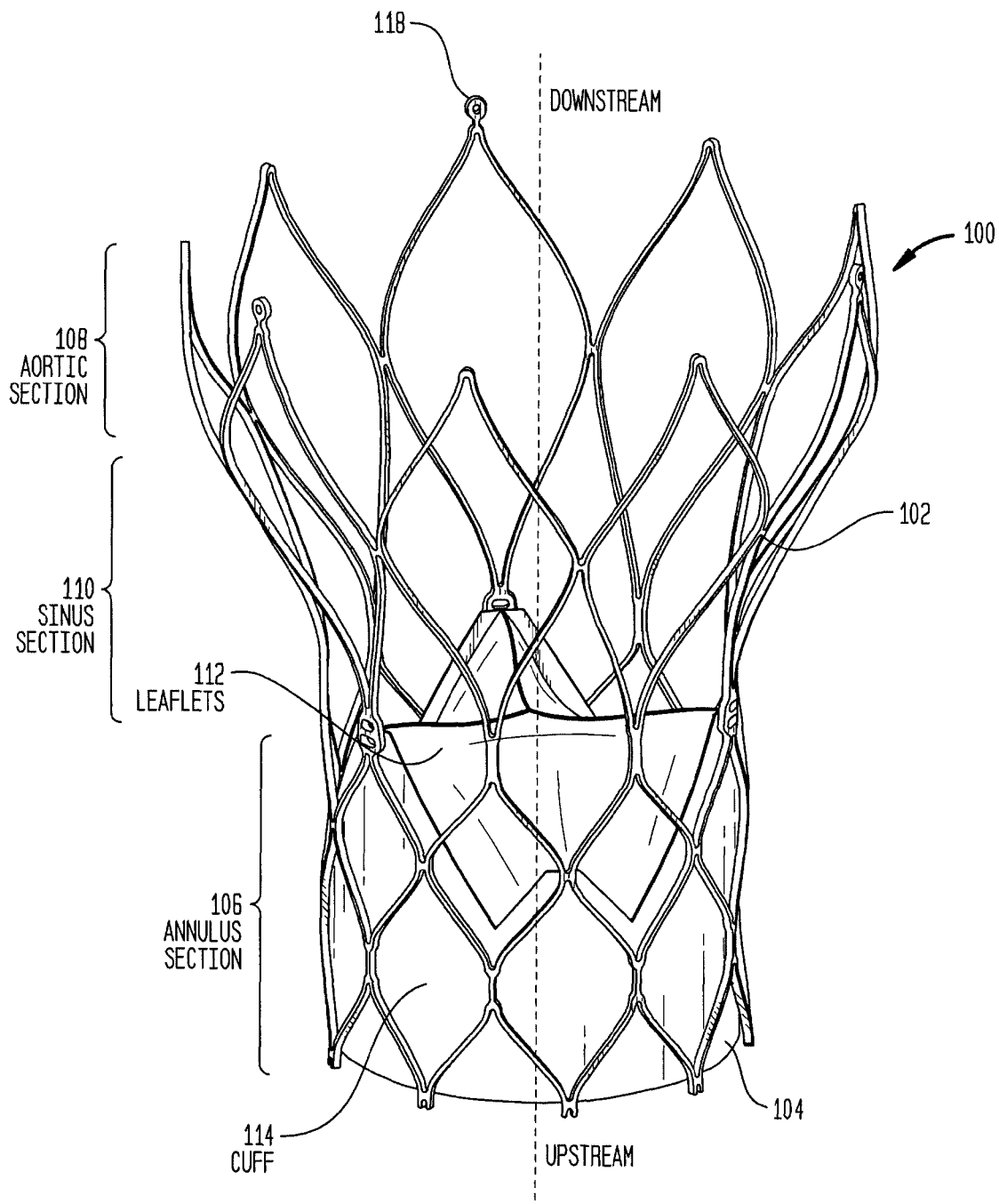

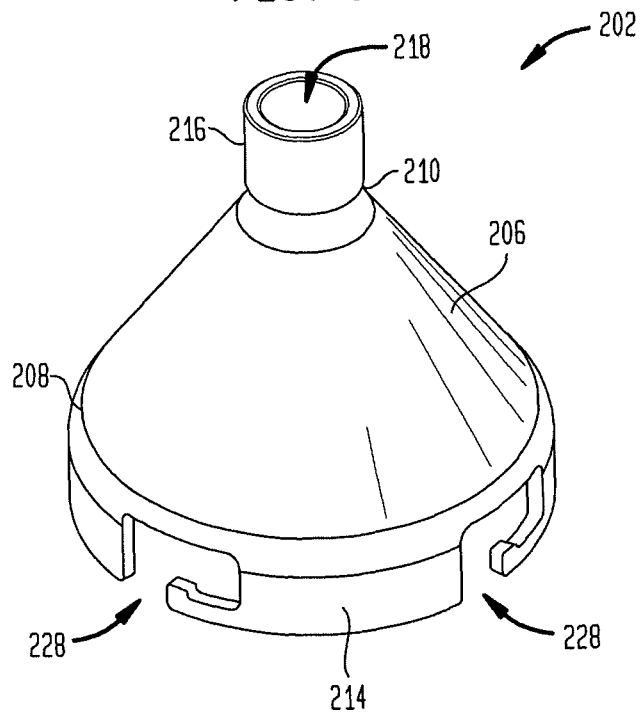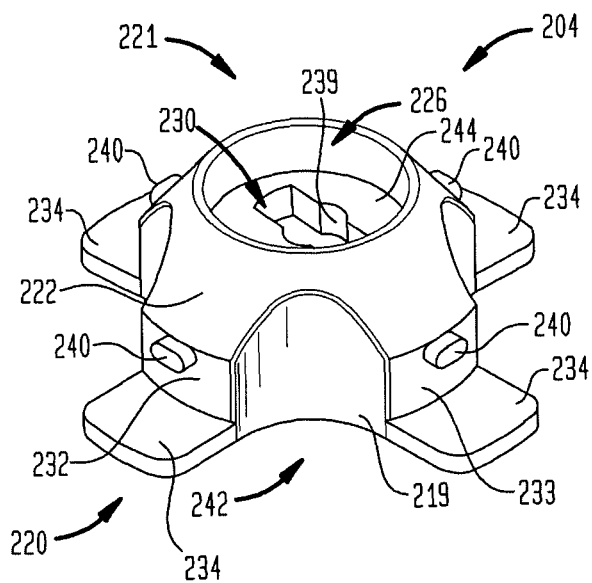

FIG. 7
FIG. 8
FIG. 9
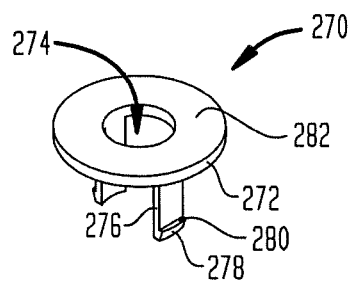
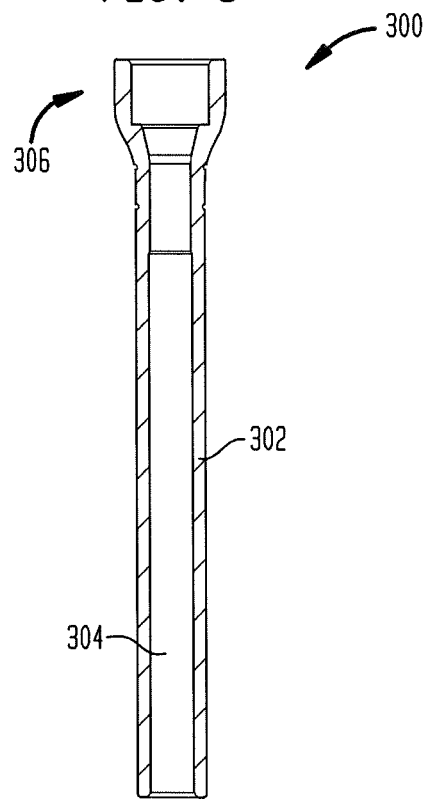
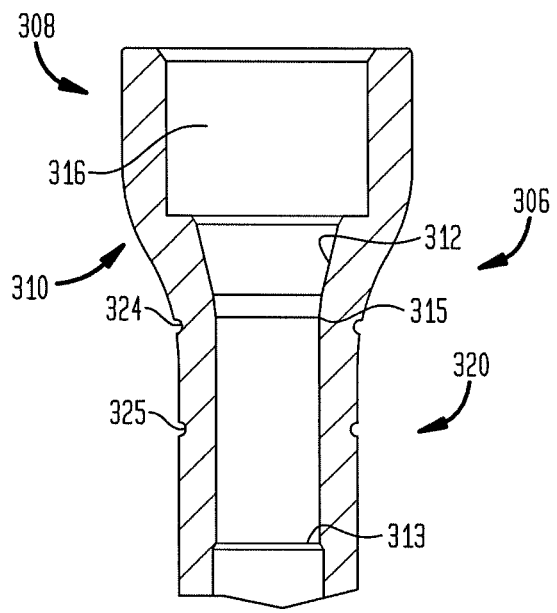

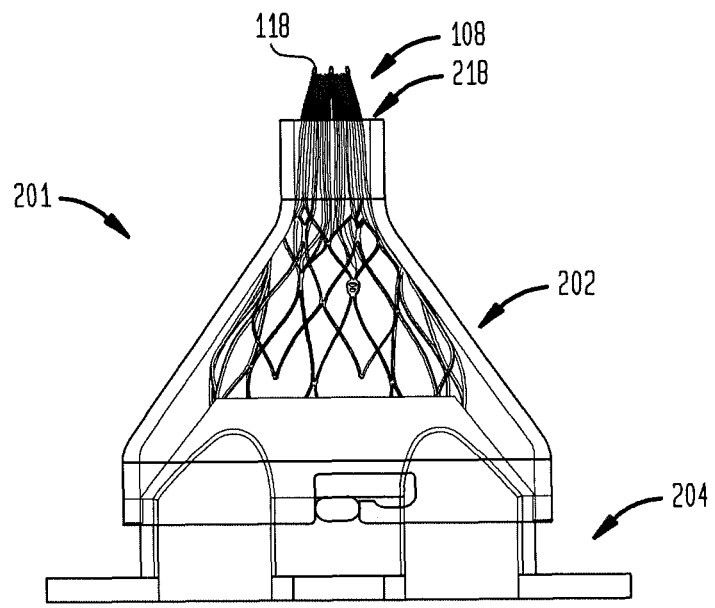
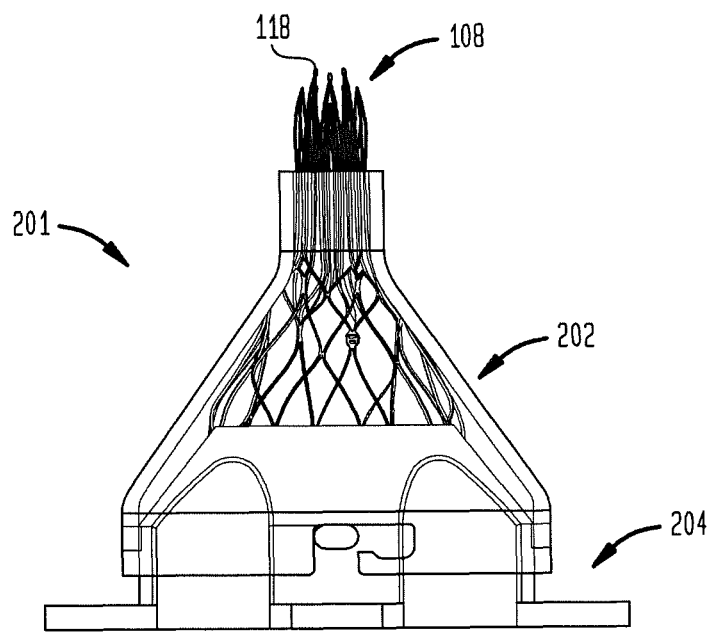

SYSTEM FOR LOADING A COLLAPSIBLE HEART VALVE

CROSS-REFERENCE TO RELATED APPLICATIONS

This application claims the benefit of the filing date of U.S. Provisional Patent Application No. 61/512,637, filed Jul. 28, 2011, the disclosure of which is hereby incorporated herein by reference.

BACKGROUND OF THE INVENTION

The present disclosure relates to prosthetic heart valve implantation and, more particularly, to assemblies and methods for loading a self-expanding collapsible heart valve into a delivery device.

Prosthetic heart valves may be formed from biological materials such as harvested bovine valves or pericardial tissue. Such valves are typically fitted within a stent, which may be inserted into the heart at the annulus of the compromised native valve to replace the native valve. To perform such insertion procedure using a minimally invasive technique, it is typically necessary to compress the stent to a reduced diameter for loading into the delivery device.

In the case of valves formed from biological materials, the stented valve is preferably preserved in the open condition for storage as compression of the valve material for extended periods compromises the integrity of the biological valve. It is therefore necessary to crimp the valve, or reduce its diameter for loading in the delivery device, in the operating arena.

Present crimping devices and methods for collapsing a stented valve, including direct radial assemblies, have proven to be unsatisfactory as they include bulky assemblies, are difficult to master, are time consuming, impart undue stress on the stented valve, or exhibit other undesirable qualities. Moreover, it is sometimes difficult to securely engage the stent to the retaining element of a delivery device. It would therefore be beneficial to provide a device and method for collapsing a stented bioprosthetic heart valve using apparatus and techniques that overcome the deficiencies of conventional devices. In addition, such devices and methods could be useful in the loading of the collapsed stented valve into a minimally invasive delivery device.

BRIEF SUMMARY OF THE INVENTION

One aspect of the present invention provides assemblies for loading a self-expanding prosthetic heart valve into a delivery device. The assembly may include a compression member having a first open end with a first diameter, a second open end with a second diameter less than the first diameter, and a wall which decreases in diameter from the first open end to the second open end, the wall defining an open space adapted to receive the heart valve; a support member having a base on a first end and a recess on a second end, the recess having a fixed depth between a support surface of the recess and an open end of the recess, the recess being adapted to receive an end of the heart valve, the support member and the compression member being movable relative to one another between an initial position in which the base of the support member is relatively far from the first open end of the compression member and an operative position in which the base of the support member is relatively close to the first open end of the compression member, wherein movement of the support member and the compression member from the initial position to the operative position pushes the heart valve through the open space such that the heart valve is radially compressed by the tapered wall of the compression member as the heart valve advances through the open space; a constricting member having a first end and a second end, the second end of the constricting member being sized to receive the compressed heart valve from the second open end of the compression member; and a spacer adapted for assembly in the recess so that the recess has a depth between a support surface of the spacer and the open end of the recess which is less than the fixed depth.

The assembly may further include a tubular extension on the second open end of the compression member, the tubular extension having a lumen therethrough; and a first seal interposed between the delivery device and the tubular extension of the compression member. The seal may include an O-ring.

The assembly may further include a locking assembly for locking the compression member to the support member. The locking assembly may include a male connecting member on one of the support member or the compression member, and a female connecting member on the other of the support member or the compression member for mating with the male connecting member. The male connecting member may include a plurality of pins extending in radial directions from the longitudinal axis of the one of the support member or the compression member, and the female connecting member may include a plurality of features on the other of the support member or the compression member adapted to mate with the plurality of pins.

Another aspect of the present invention provides methods for loading a self-expanding prosthetic heart valve into a delivery device. The delivery device may include a tip, a retaining element, a compartment defined between the tip and the retaining element and adapted to receive the heart valve, and a distal sheath movable between a closed position fully covering the compartment and an open position uncovering the compartment. The heart valve may include a stent, a valve assembly supported by the stent, and at least one retainer at one end of the stent, the heart valve having an expanded condition and a collapsed condition.

Methods according to this aspect of the present invention may include configuring a support member to receive an end of the heart valve, the support member having a base on a first end and a recess on a second end, the recess having a fixed depth between a support surface of the recess and an open end of the recess, the configuring step including assembling a spacer in the recess so that the recess has a depth between a support surface of the spacer and the open end of the recess which is less than the fixed depth; inserting the end of the heart valve in the expanded condition into the recess of the support member; advancing the support member and a compression member toward one another, the compression member having an inner surface which decreases in diameter uniformly from a first open end to a second open end, the advancing step including advancing the heart valve through the compression member until the at least one retainer protrudes from the second open end of the compression member; positioning the delivery device in an initial position in a constricting member, the constricting member having a first end, a second end and an elongated tubular portion between the first end and the second end, the delivery device in the initial position having the distal sheath in the open position and the retaining element positioned outside the constricting member; attaching the at least one retainer of the heart valve to the retaining element of the delivery device; and moving the distal sheath of the delivery device to the closed position during which the heart valve is advanced through the second open end of the compression member and into the elongated tubular portion of the constricting member to place the heart valve in the collapsed condition.

The method may further include filling at least a portion of the compression member with a sterile liquid before moving the distal sheath of the delivery device to the closed position to remove air from the heart valve and the delivery device.

Yet another aspect of the present invention provides a kit for delivering a self-expanding prosthetic heart valve to an implantation site in a patient, the heart valve being one of a plurality of different sizes. The kit may include a delivery device including a tip, a retaining element, a compartment defined between the tip and the retaining element and adapted to receive the heart valve, and a distal sheath movable between a closed position fully covering the compartment and an open position uncovering the compartment. The kit may further include a compression member, a support member, a constricting member and a spacer as described above. The fixed depth of the recess may be adapted for use with a heart valve of a first length, and the second depth of the recess may be adapted for use with a heart valve having a length less than the first length. The kit may include a plurality of spacers adapted for assembly in the recess, each spacer being adapted to reduce the depth of the recess by a selected amount, the selected amount for one spacer being different from the selected amount for each of the other spacers.

BRIEF DESCRIPTION OF THE DRAWINGS

Various embodiments of the present loading assembly are disclosed herein with reference to the drawings, wherein:

FIG. 4 is a perspective view of a self-expanding prosthetic heart valve;

FIG. 5 is a perspective view of a compression member for use in the present invention;

FIG. 6A is a perspective view of a support member for use in the present invention;

FIG. 7 is a perspective view of a spacer for use in the present invention;

FIG. 8 is a longitudinal cross-sectional view of a constricting member for use in the present invention;

FIG. 9 is an enlarged longitudinal cross-sectional view of an end section of the constricting member of FIG. 8;

FIGS. 11-20 illustrate the steps of a method for loading a prosthetic heart valve into a delivery device using the loading assembly of FIG. 10.

DETAILED DESCRIPTION

Figure 1:
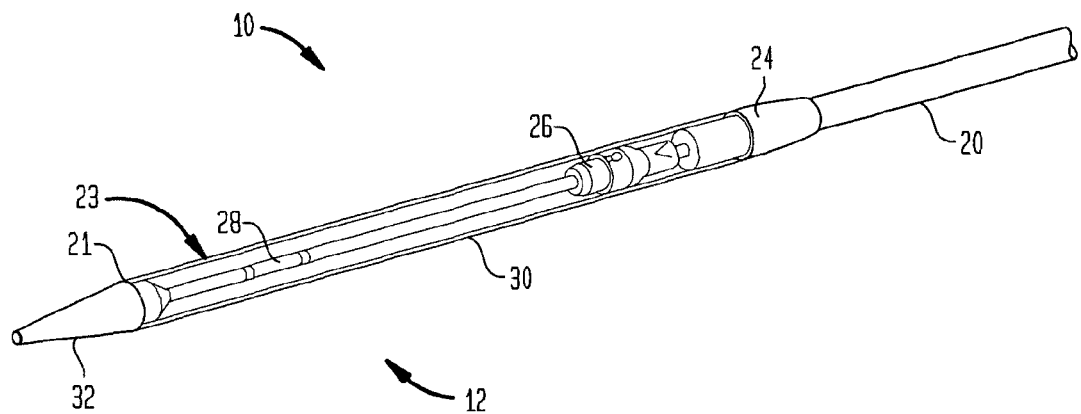
FIG. 1 is a perspective view of a distal portion of a delivery device.

Embodiments of the presently disclosed loading assemblies are described herein in detail with reference to the drawing figures, wherein like reference numerals identify similar or identical elements. In the drawings and in the description which follows, the term "proximal" refers to the end of the catheter assembly, or portion thereof, which is closest to the operator in use, and to the end of the loading assembly which is closest to the proximal end of the catheter assembly when the loading assembly is assembled on the catheter assembly during a valve loading procedure. The term "distal" refers to the end of the catheter assembly, or portion thereof, which is farthest from the operator in use, and to the end of the loading assembly which is closest to the distal end of the catheter assembly when the loading assembly is assembled on the catheter assembly during a valve loading procedure.

The present disclosure relates to assemblies and methods for loading a self-expanding stent or a collapsible prosthetic heart valve into a minimally invasive delivery device. An exemplary minimally invasive delivery device 10 is illustrated in FIGS. 1 and 2.

Figure 2:
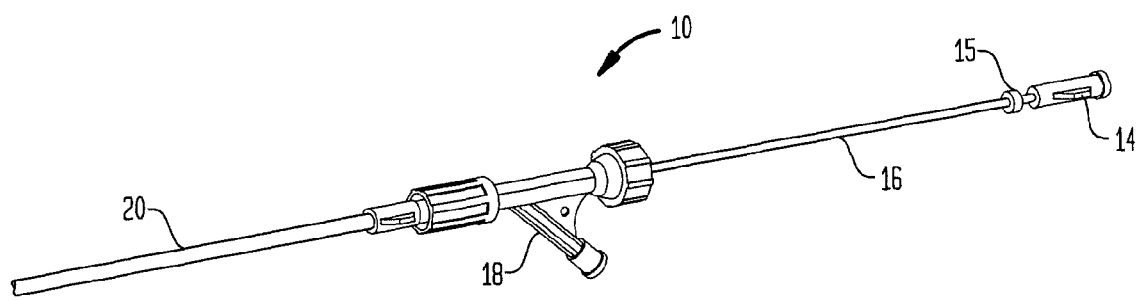
FIG. 2 is a perspective view of a proximal portion of the delivery device of FIG. 1.

As seen in FIGS. 1 and 2, an exemplary delivery device 10 for transfemoral delivery of a collapsible prosthetic heart valve (or other types of self-expanding collapsible stents) has a catheter assembly 12 for delivering the heart valve to and deploying the heart valve at a target location. The catheter assembly 12 includes a compartment 23 defined between an atraumatic tip 32 of the delivery device 10 and a retaining element 26. A support shaft 28 is connected between tip 32 and retaining element 26 and defines the length of compartment 23. A distal sheath 30 is slidably arranged relative to the compartment 23 so that, in a distalmost or closed position in which the distal end 21 of the sheath abuts atraumatic tip 32, the sheath covers the prosthetic heart valve and retains it for delivery to the target site, and in a proximal or open position in which the distal end 21 of the sheath is spaced from the atraumatic tip 32, the sheath uncovers the prosthetic heart valve for deployment at the target site.

An inner tube 16 having a lumen therethrough extends from a hub 14 at or near its proximal end to a distal end which may be connected to retaining element 26. Optionally, the distal end of inner tube 16 may extend through retaining element 26 and support shaft 28 for connection to atraumatic tip 32. In either arrangement, the distal end of inner tube is connected to compartment 23 so as to define a fixed distance between hub 14 and the compartment. The lumen through inner tube 16 is sized to slidingly receive a guidewire (not shown) for use in guiding the delivery device to the target site. At its proximal end, inner tube 16 may be provided with a hemostasis valve (not shown) for preventing, or at least hindering, blood flow out from the inner tube.

Hub 14 is adapted for connection to another system or mechanism, such as an operating handle (not shown) for displacing the distal sheath 30. Mechanisms for displacing the distal sheath 30 between its proximal and distal positions are described in International Patent Application Publication No. WO/2009/091509, the disclosure of which is hereby incorporated by reference herein. A retaining ring 15 may be mounted on the inner tube 16 near hub 14.

Catheter assembly 12 further includes an outer shaft 20 which is connected at its distal end through a tapered transition member 24 to the proximal end of distal sheath 30, and at its proximal end to the operating handle (not shown). A Y-connector 18 may also be connected at the proximal end of outer shaft 20, and may include a hemostasis valve for hindering blood flow out from between the inner tube 16 and the outer shaft 20. The Y-connector 18 may also be coupled to a fluid source for flushing the outer shaft 20, injecting contrast media during a prosthetic valve implantation procedure, and the like.

Figure 3:
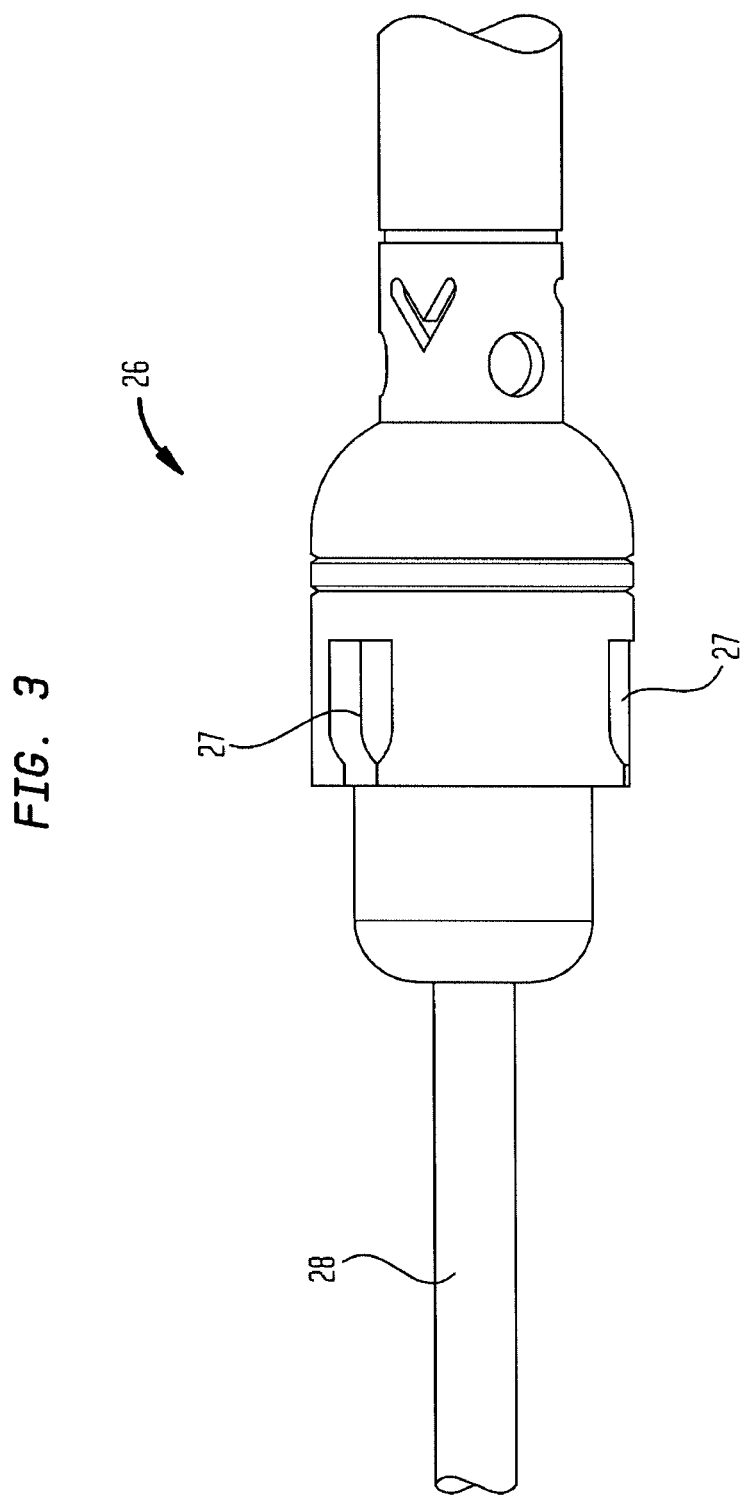
FIG. 3 is an enlarged side view of a retaining element of the delivery device shown in FIGS. 1 and 2.
Figure 6B:
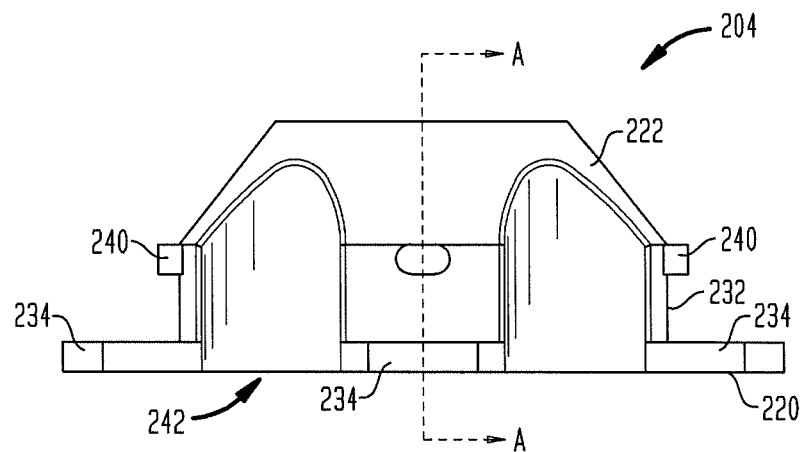
FIG. 6B is a side elevational view of the support member of FIG. 6A.
Figure 6C:
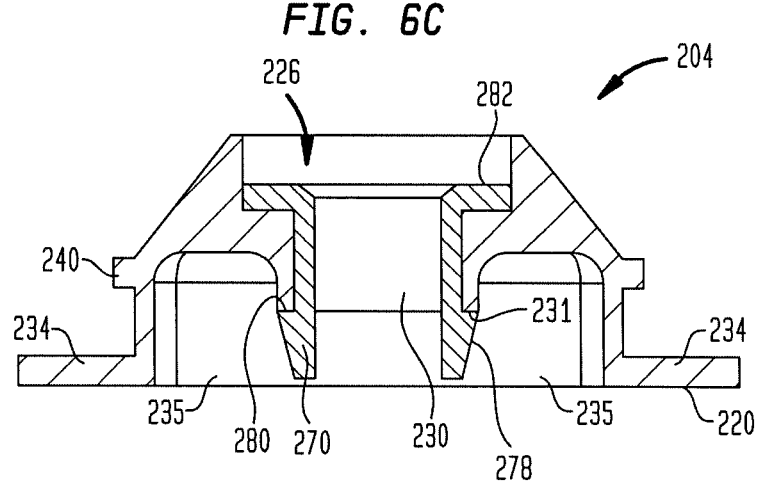
FIG. 6C is a cross-sectional view of the support member of FIG. 6A, taken along section line A-A of FIG. 6B.

As shown in FIG. 3, the retaining element 26 may include a plurality of recesses 27 located around its periphery. The recesses 27 are spaced apart from one another and each is sized and shaped to receive a tab or retainer on one end of the prosthetic heart valve to maintain the prosthetic heart valve in assembled relationship with the delivery device 10, to minimize longitudinal movement of the prosthetic heart valve relative to the delivery device during unsheathing and resheathing procedures, to help prevent rotation of the prosthetic heart valve relative to the delivery device as the delivery device is advanced to the target site and during deployment, and to maintain the alignment of the stent cells and prevent them from becoming tangled.

FIG. 4 shows a conventional bioprosthetic valve 100 designed to replace a native aortic valve. The valve 100 has a collapsed condition and an expanded condition and may be formed from a collapsible framework or stent 102, with a valve assembly 104 internally connected to the stent. The stent 102 may be formed from any suitable biocompatible material, such as nitinol or any other suitable elastic or shape memory material, and may include an annulus section 106, an aortic section 108, and a sinus section 110 located between the annulus section and the aortic section. The aortic section 108 may have a larger cross-section than the annulus section 106. The valve assembly 104 conventionally includes a plurality of leaflets 112 and a cuff 114 attached to the stent 102. The leaflets 112 and the cuff 114 may be formed from a biocompatible polymer, from natural tissue such as bovine or porcine pericardial tissue, or from other appropriate biocompatible materials. The valve assembly 104 is preferably connected to the stent 102 generally within the annulus section 106. The valve 100 may include a plurality of tabs or retainers 118 at spaced positions around one or both ends of the stent 102 for engagement with the retaining elements 26 of the delivery device 10 as described above. The retainers 118 may also be utilized to collapse the valve 100 for loading into the delivery device 10, as will be discussed below.

Valves 100 may be provided in a number of different diameters depending upon the anatomy of the patient into which the valve is to be implanted. As a result of its construction, the stent 102 of the valve will generally elongate as the valve is crimped to its collapsed condition. The amount of elongation generally will be directly related to the diameter of the stent. Thus, for larger diameter stents, the amount of elongation will be greater than that for smaller diameter stents. The present invention accommodates this difference in elongation as the heart valve is collapsed and loaded into delivery device 10.

The valve 100 is preferably stored in its expanded or open condition as the bioprosthetic valve assembly 104 may be compromised by storage in a collapsed condition for extended periods of time. As such, it is necessary to crimp the valve 100 into a collapsed condition of reduced cross-section for loading into the delivery device 10 at the latest possible time prior to the surgical implantation procedure. In order to effectively limit the time period the valve 100 is collapsed, the crimping process is preferably conducted in the operating arena by the surgeon, interventional cardiologist or surgical assistant using a specialized assembly.

FIGS. 5-8 illustrate a loading assembly 200 according to an embodiment of the present invention, the loading assembly generally including a compression member 202 and a support member 204 adapted to be coupled to one another, a constricting member 300 and a spacer 270. The compression member 202 includes a funnel 206 having a substantially frusto-conical shape with a large diameter at a first end 208 and a smaller diameter at a second end 210. The diameter of the funnel 206 may decrease uniformly from the first end 208 to the second end 210 to compress the valve 100 as it is advanced through the compression member 202. The compression member 202 is preferably made of a substantially rigid material, and may be wholly or partly made of a transparent plastic, such as polycarbonate or acrylic, to allow viewing of the valve 100 during loading.

The compression member 202 may further include an annular rim 214 extending from the first end 208 of the funnel 206 for joining the compression member to the support member 204 as described below. The rim 214 may include a plurality of slots 228 disposed around its outer periphery. While the drawings show slots 228 that are substantially P-shaped, the slots may have any other shapes suitable for securely holding the compression member 202 to the support member 204. The rim 214 may include four such slots 228, or more or less than four. Regardless of the number or slots 228, adjacent slots are preferably spaced equidistantly from each other.

The compression member 202 also may include a tubular extension 216 projecting from the second end 210 of the funnel 206. The tubular extension 216 has an opening 218 therethrough in communication with the interior of funnel 206. The opening 218 is sized and shaped to receive the distal sheath 30 of the delivery device 10 therein. The cross-section of the tubular extension 216 is preferably substantially circular, but may be oblong, oval, elliptical, or polygonal.

With reference to FIGS. 6A, 6B, 6C and 10, the support member 204 is preferably made in whole or in part of a substantially rigid material, and includes a body 219 having a substantially flat or planar bottom support surface 220 and a top end 221. Body 219 has an outer wall 232 and a generally rectangular aperture 230 extending therethrough. Aperture 230 has a generally cylindrical central portion 239 sized and shaped to receive at least a portion of the tip 32 of the delivery device 10 therein. A recess 226 extends downwardly from the top end 221 of the body 219 concentrically with bore 230 so as to define a support surface 244 at a spaced distance from the top end. Recess 226 has a diameter and a depth defined by support surface 244 sufficient to receive at least a portion of the annulus section 106 of the stent 102 in an expanded condition.

The outer wall 232 of body 219 does not extend continuously around the body, but rather may be interrupted by a plurality of inwardly curved indentations 242 which divide the outer wall into a plurality of wall segments 233, only two of which are shown in FIG. 6A. Although FIG. 6A depicts a support member 204 having four indentations 242 evenly spaced around the periphery of body 219, it is contemplated that the support member may be provided with more or less than four such indentations. Indentations 242 facilitate the grasping of support member 204. Between indentations 242, that is, in the space between outer wall segments 233 and bore 230, body 219 may include a plurality of recesses 235 extending inwardly from the bottom support surface 220. Recesses 235 reduce the mass of body 219 and facilitate the manufacturing process by eliminating excessively thick portions of the body.

The outer wall segments 233 of body 219 do not extend all the way to the top end 221 of the body, but rather terminate at their top ends at a continuous wall 222 oriented at an oblique angle to the outer wall 232. At their bottom ends, outer wall segments 233 each include a radially projecting supporting plate 234, the bottom surfaces of which are substantially coplanar with the bottom support surface 220 of body 219. At least one pin 240 may protrude radially outward from each outer wall segment 233. Pins 240 are preferably spaced a sufficient distance from supporting plates 234 and sized and shaped to be received in the slots 228 of the compression member 202 to join the compression member and the support member 204 together. When joined together, the compression member 202 and the support member 204 collectively define a partial loading assembly 201.

FIG. 7 illustrates a spacer 270 which optionally may be used in connection with support member 204 when a relatively small valve 100 is to be loaded into delivery device 10 using loading assembly 200. Spacer 270 has a generally flat annular portion 272 with a central aperture 274 sized and shaped to receive at least a portion of the tip 32 of the delivery device 10 therethrough. Each leg in a pair of resilient legs 276 has a tapered surface 278 adjacent its free end which terminates at a spaced distance from the free end in a retention surface 280. Spacer 270 may be used to reduce the overall depth of the recess 226 in support member 204. Thus, spacer 270 may be inserted into recess 226 with legs 276 projecting into aperture 230. As spacer 270 is pushed downwardly toward support surface 244, the tapered surfaces 278 adjacent the free ends of legs 276 will contact the narrow sides of aperture 230, causing legs 276 to flex inwardly until retention surfaces 280 engage with a bottom edge 231 of aperture 230 or other structures in the aperture 230 to cause spacer 270 to lock in place. The top surface of annular portion 272 will thus present a new support surface 282 for the annulus section 106 of the stent 102 during a valve-loading procedure. The new support surface 282 will be spaced from the support surface 244 of recess 226 by the thickness of annular portion 272. Support surfaces 244 and 282 may be marked with a size or other indicia (not shown) indicating the size of the valve that support surface is intended to be used with.

FIGS. 8 and 9 illustrate a constricting member 300 designed to minimize the flaring of the distal end 21 of the distal sheath 30 during loading of a prosthetic heart valve into the compartment 23 of delivery device 10. The constricting member 300 may be wholly or partly made of a transparent plastic, such as polycarbonate or acrylic, to allow viewing of the delivery device 10 during loading and includes a tubular member 302 having a central lumen 304 sized and shaped to slidingly receive at least the distal sheath 30 of the delivery device 10.

As seen in FIG. 9, at one end 306, the constricting member 300 may have an enlarged head 308 with a counterbore 316 formed therein. The counterbore 316 may have a diameter that is larger than the diameter of lumen 304, and in particular, may be sized and shaped to receive the tubular extension 216 of the compression member 202. Preferably, the diameter of counterbore 316 is only slightly larger than the outer diameter of the tubular extension 216 so as to create a friction fit therebetween.

Between the tubular member 302 and the enlarged head 308, constricting member 300 may have a tapered portion 310. In particular, tapered portion 310 may have an inner surface 312 which tapers from a larger diameter at its end adjacent the counterbore 316 to a smaller diameter at its other end to help compress valve 100 further during loading into delivery device 10.

The constricting member 300 may further include a transition portion 320 disposed between the tapered portion 310 and the tubular member 302. The transition portion 320 may have a substantially constant inner diameter sized and shaped to receive at least the distal sheath 30 of the delivery device 10. The inner diameter of the transition portion 320 may be slightly smaller than the diameter of lumen 304 and slightly larger than the outer diameter of the distal sheath 30 in order to substantially prevent or minimize the flaring of the distal end 21 of the distal sheath 30 while the valve 100 is loaded in the delivery device 10, as discussed in detail below. The larger diameter of the lumen 304 allows a user to easily slide the constricting member 300 over the distal sheath 30 of the delivery device 10. In a variant hereof, the transition portion 320 may have an inner diameter which tapers downwardly from a slightly larger diameter at an end 313 thereof to a slightly smaller diameter at an end 315 thereof to accommodate small variations in the outer diameter of the distal sheath 30.

An annular groove or other indicator line 324 may extend partly or entirely around the outer periphery of the tubular member 302 at the junction between the tapered portion 310 and the transition portion 320. Another annular groove or indicator line 325 may extend partly or entirely around the outer periphery of the tubular member 302 at a spaced distance from the first line 324. Lines 324 and 325 mark the area in which the user should place the distal end 21 of the distal sheath 30 during the loading procedure. As discussed in detail below, using the constricting member 300 to help load the valve 100 into the delivery device 10 reduces the loading forces (i.e., the forces required to load the valve into the delivery device) and reduces flaring of the distal end 21 of the distal sheath 30.

Figure 10:
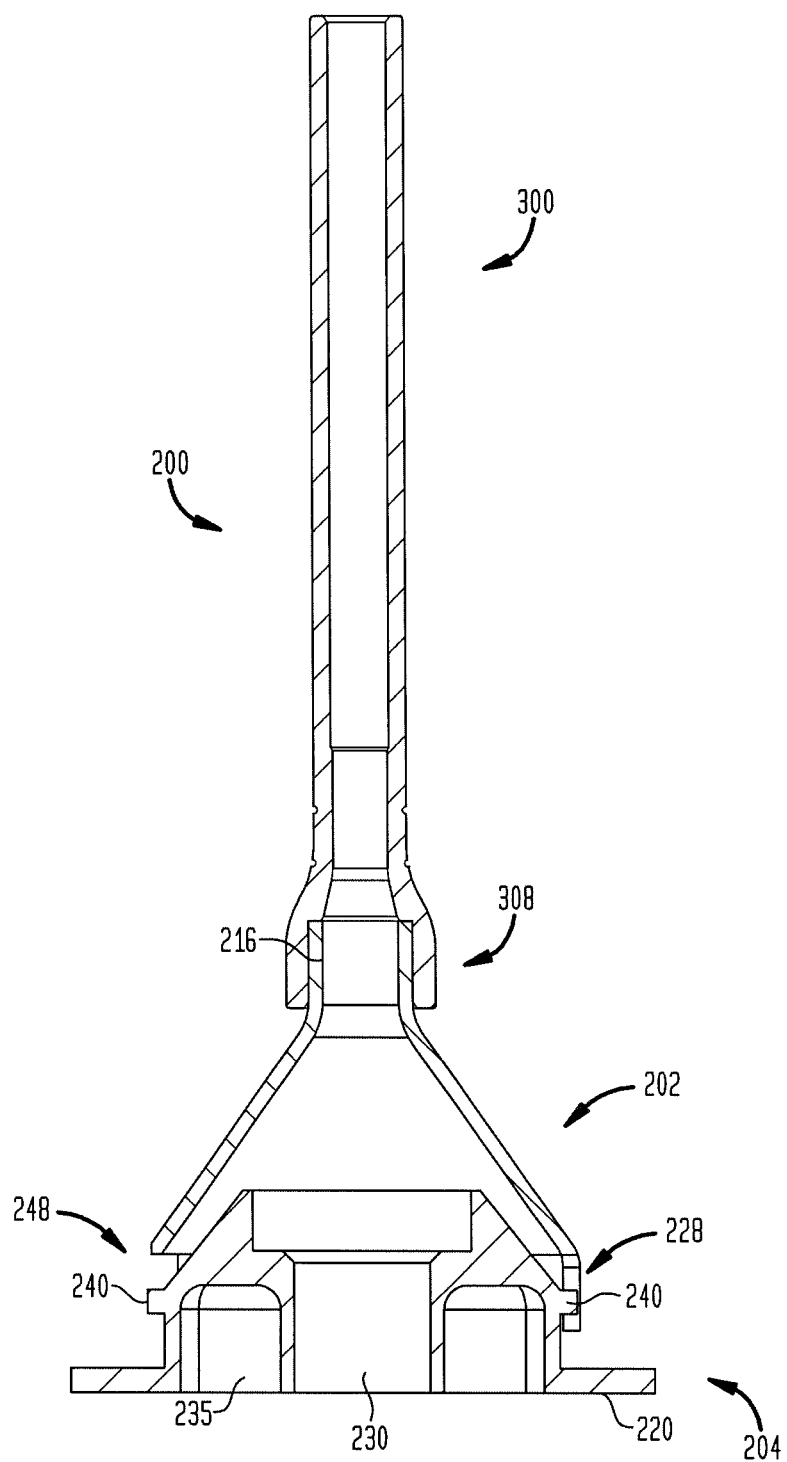
FIG. 10 is a longitudinal cross-sectional view of a loading assembly for use in the present invention, including the compression member of FIG. 5, the support member of FIG. 6A, and the constricting member of FIG. 8.

FIG. 10 shows an assembled loading assembly 200 including the compression member 202 of FIG. 5, the support member 204 of FIG. 6 and the constricting member 300 of FIG. 8. As seen in FIG. 10, the constricting member 300 is connected by its enlarged head 308 to the tubular extension 216 of the compression member 202, and the compression member 202 is locked to the support member 204. To lock the compression member 202 to the support member 204, the pins 240 of the support member are inserted into the slots 228 of the compression member, and the compression member is turned relative to the support member to slide the pins toward the closed ends of the slots. Hence, the pins 240 and the slots 228 together form a locking mechanism 248. Rather than the engagement of the pins 240 in the slots 228, it is contemplated that any other known locking mechanisms may be employed to securely lock the compression member 202 to the support member 204.

Figure 11:
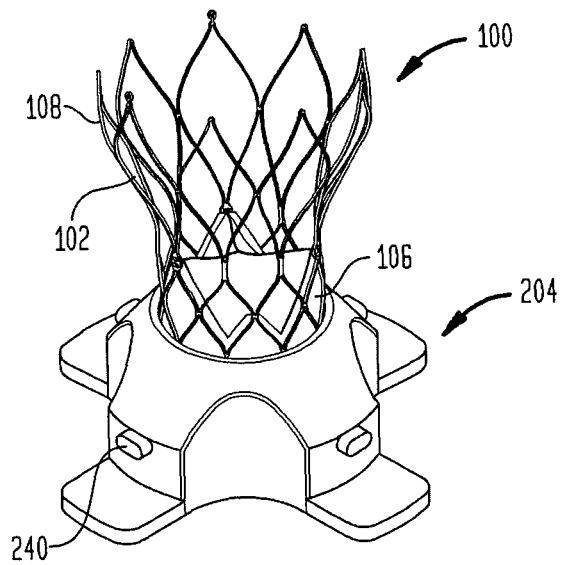
Figure 12:
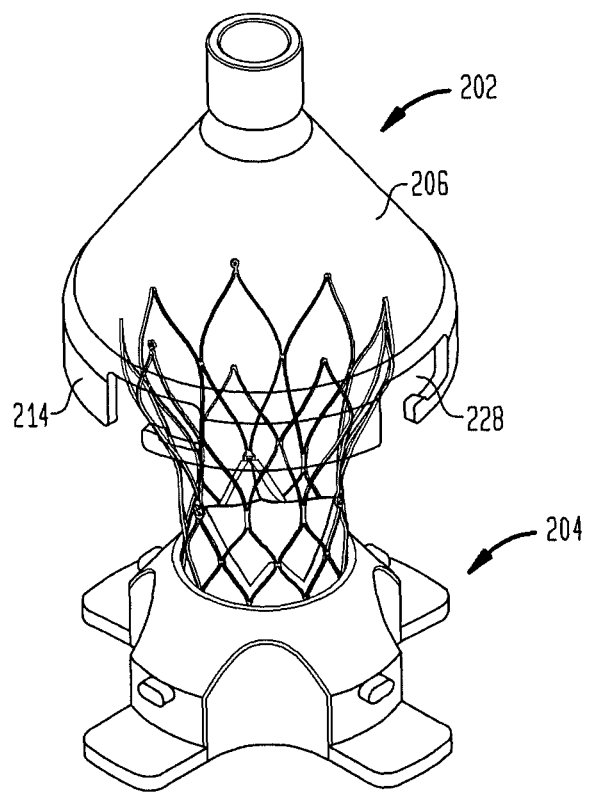

As seen in FIGS. 11-20, the loading assembly 200 may be used to load the collapsible prosthetic heart valve 100 into a delivery device 10. Where a relatively small heart valve 100 is to be implanted, the spacer 270 is first assembled in the recess 226 of the support member 204 to decrease the overall depth of the recess. Then, as shown in FIG. 11, with the support member 204 on a flat surface, at least a portion of the annulus section 106 of the stent 102 may be placed within the recess 226 of the support member until the end of the stent contacts support surface 282 on spacer 270. The compression member 202 may then be placed over the aortic section 108 of the stent 102 so that the aortic section of the stent is positioned within the funnel 206, as depicted in FIG. 12. As shown in FIG. 13, the compression member 202 and the support member 204 may then be pushed together, the tapered walls of the funnel 206 gradually compressing the valve 100 until a portion of the aortic section 108 of the stent 102 is forced into and through the opening 218 of the compression member. When a portion of the aortic section 108 of the stent 102 passes through the opening 218 of the compression member 202, the retainers 118 of the stent will protrude through the opening 218 and will be positioned closely adjacent to one another. Even though the heart valve being compressed is relatively small, the use of spacer 27 reduces the overall depth of recess 226 such that the retainers 118 of stent 102 will protrude from opening 218 when the stent is collapsed. At this point, the pins 240 of the support member 204 will be positioned within the slots 228 of the compression member 202, and the members may be locked together by rotating the support member relative to the compression member, such that the pins 240 of the support member slide toward the closed ends of the slots 228 of the compression member.

Figure 15A:
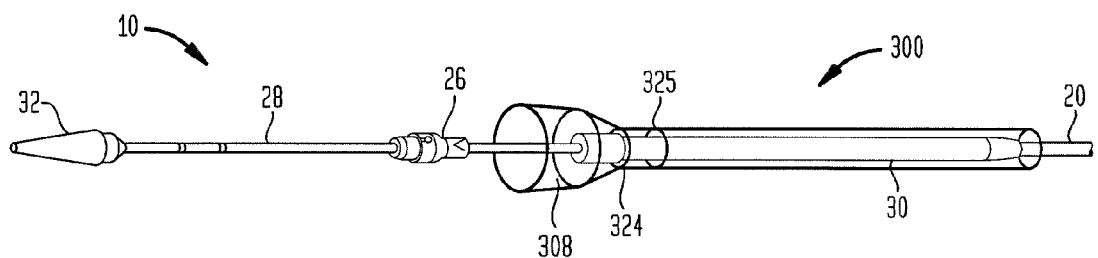

As seen in FIG. 15A, with the distal sheath 30 in a proximal or open position, the constricting member 300 may be placed over the delivery device 10 with the enlarged head 308 positioned closer to the tip 32 than to the hub or handle of the delivery device, and with the distal end 21 of the distal sheath 30 longitudinally positioned between indicator lines 324 and 325 of the constricting member. It will be appreciated that the constricting member 300 also may be placed over the delivery device 10 with the distal sheath 30 in the distalmost or closed position, and that the distal sheath subsequently may be moved to the proximal or open position.

Figure 15B:
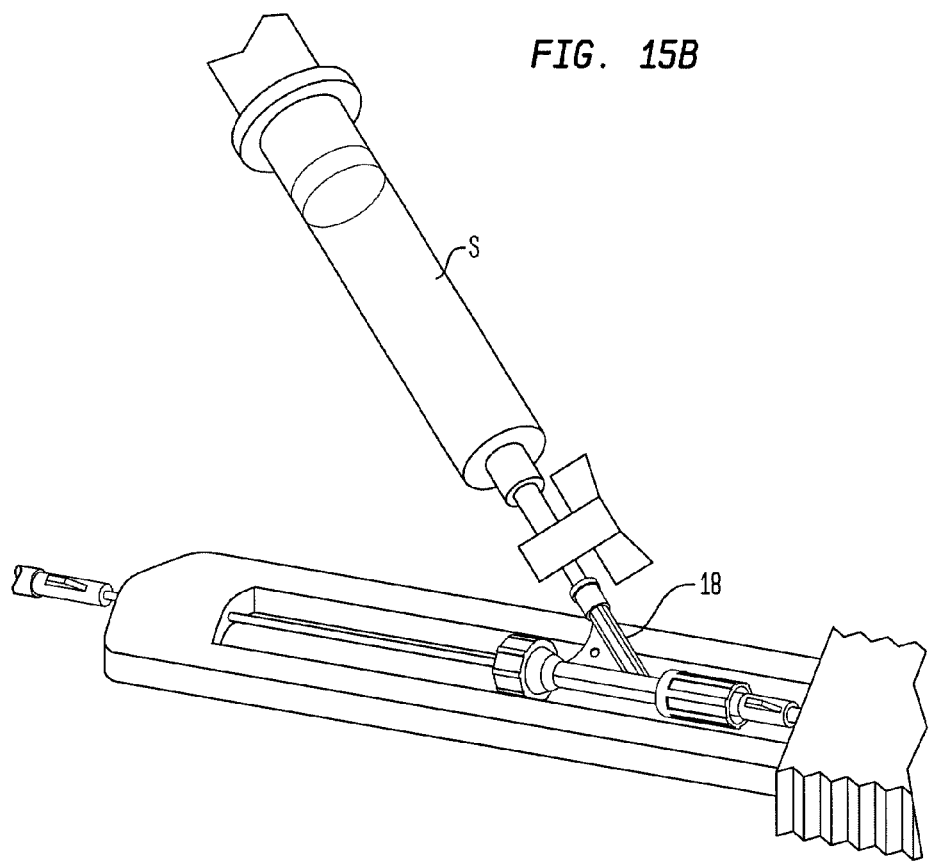

Before loading the valve 100 into the delivery device 10, it is preferable to subject the delivery device to a deairing process. In that regard, with the constricting member 300 assembled over the distal sheath 30 and the distal sheath in an open position, a syringe S may be connected to the Y-connector 18 of the delivery device 10, as shown in FIG. 15B. The syringe may be used to inject a sterile liquid, such as saline, into the proximal end of the delivery device and out through the open compartment 23, thereby flushing the air from the device. During this flushing step, the distal end of the delivery device may be tapped multiple times to facilitate the air removal.

Figure 16:
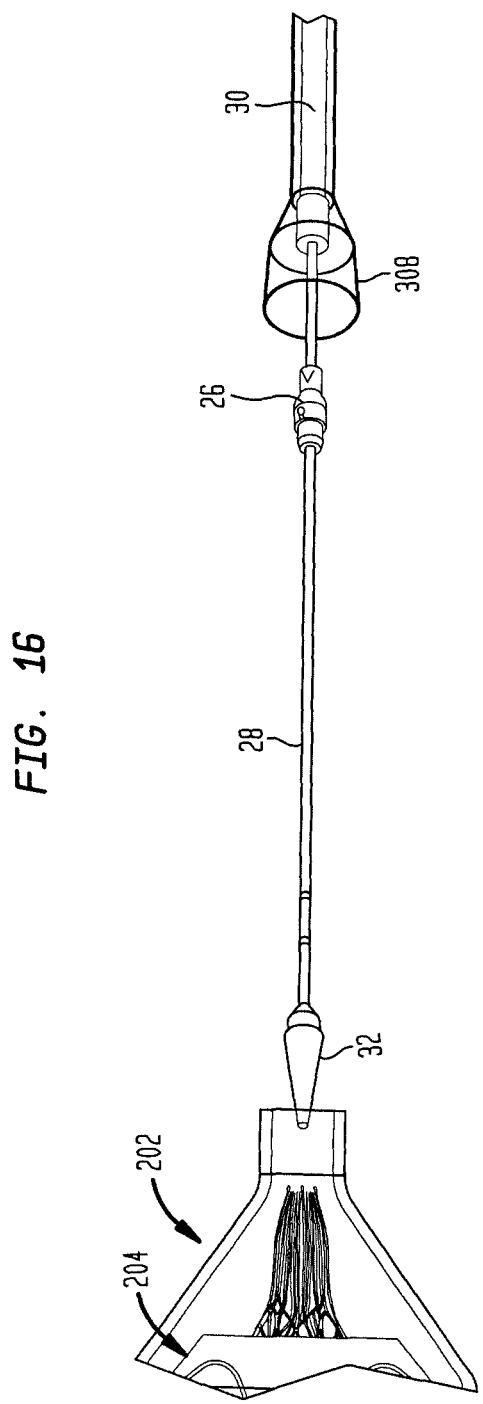
Figure 17:
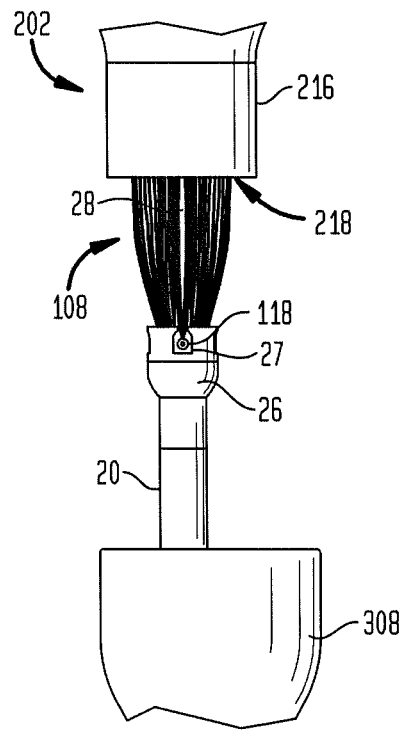

Once flushing of the delivery device 10 has been completed, the tip 32 and the support shaft 28 of the delivery device 10 may be inserted into the end of the collapsed valve 100 protruding from the opening 218 of the compression member 202. To accomplish this, the compression member 202 and the support member 204 may be squeezed closer together. (The dimension of the slots 228 in the longitudinal direction, i.e., the height of the slots, is greater than the dimension of the pins 240 in the longitudinal direction, i.e., the height of the pins. Therefore, even though the compression member 202 and the support member 204 are assembled together, they still may move further toward one another.) As the compression member 202 and the support member 204 move closer together, a greater portion of the stent 102 is forced out through opening 218, causing the retainers 118 to begin to separate from one another, as illustrated in FIG. 14. The tip 32 and support shaft 28 of the delivery device 10 may then be inserted between the retainers 118 and into the end of the collapsed valve 100, as shown in FIG. 16. The partial loading assembly 201 then may be advanced along the support shaft 28 until the retainers 118 of the stent 102 are positioned over the retaining element 26 of the delivery device 10. The partial loading assembly 201 may be twisted as needed to align the retainers 118 with the recesses 27 in the retaining element 26. Positioning the retainers 118 within the recesses 27 of the retaining element 26 attaches the stent 102 to the delivery device 10, as seen in FIG. 17. With the stent 102 attached to the retaining element 26, the constricting member 300 and the distal sheath 30 may be slid together toward the partial loading assembly 201 (or the inner tube 16 may be moved proximally relative to the constricting member 300 and the distal sheath 30) to about the position shown in FIG. 18, in which the distal sheath covers the retainers 118 of the stent, at the same time maintaining the distal end 21 of the distal sheath between indicator lines 324 and 325. The tapered inner surface 312 of the enlarged head 308 facilitates the compression of the stent 102 as it moves into the constricting member 300. When the constricting member 300 and the partial loading assembly 201 are close together, they may be joined to one another by assembly of the enlarged head 308 of the constricting member 300 to the tubular extension 216 of the compression member 202.

Figure 18:
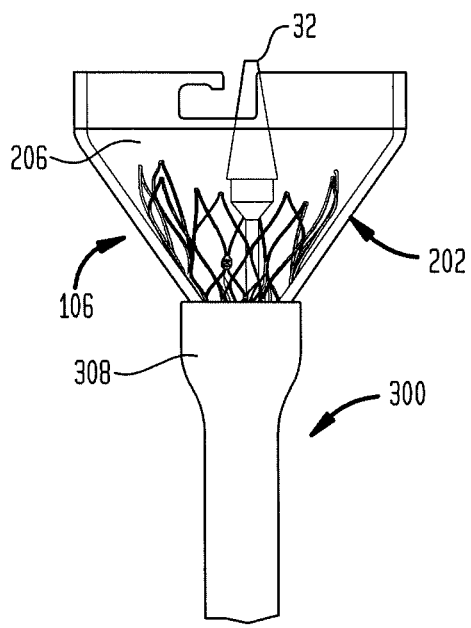

In order to deair the valve 100, a sterile liquid, such as saline, may be dispensed into the compression member 202 through its first open end 208. To do so, the support member 204 may be disassembled from the compression member 202 by first rotating the support member relative to the compression member, such that the pins 240 of the support member slide toward the open ends of the slots 228 of the compression member. This action unlocks the members from one another. The support member 204 may then be moved away from the compression member 202 to disassemble the partial loading assembly 201. With the first open end 208 of the funnel 206 facing up, the sterile liquid may be dispensed into the compression member 202 through the first open end. The sterile liquid may be dispensed into the compression member 202, such as through a syringe or a sterile container, until the funnel 206 is substantially filled, as shown in FIG. 18. The syringe may need to be refilled several times during the injection process in order to fill the funnel 206 with the sterile liquid.

Any air bubbles in the sterile liquid within the funnel 206 may then be removed. It is important that little or no air be released into the human body during deployment and/or resheathing of the valve within the human heart, as the air may block vascular flow and cause tissue damage. For this reason, it is important to remove air bubbles from the delivery device 10 and the valve 100 before introducing them into the body. Testing has shown that, if the methods and assemblies described in this application are employed, minimal air will be released into the patient's bloodstream during valve deployment and resheathing.

Figure 19:
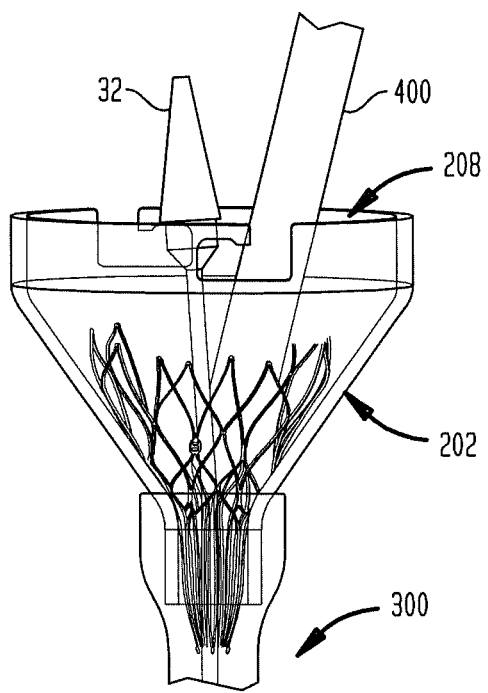

Air bubbles formed in the sterile liquid near the space between the leaflets 112 and the cuff 114 of the valve 100 may be removed by using a tube or rod 400 or any other suitable atraumatic probe. The tube 400 is commonly known in the art as a "leaflet tester" and may be formed of a substantially soft material, such as a soft polymer. In order to remove the air bubbles from the sterile liquid, the tube 400 may be placed into the sterile liquid contained in the funnel 206 of the compression member 202 and used to probe areas of potential air entrapment, including gently agitating the liquid, as shown in FIG. 19. A syringe may be used to remove the air bubbles from the space near the retaining element 26 of the delivery device 10. To do so, the syringe may be inserted into the space near the retaining element 26, and the sterile liquid near the retaining element 26 may be gently agitated with the syringe. After the air bubbles have been removed, the valve 100 may be pulled into the distal sheath 30 until the valve is completely covered, as seen FIG. 20. The constricting member 300 and the compression member 202 may then be removed from the delivery device 10. The inner tube 16 of the delivery device 10 may then be flushed with any suitable sterile liquid using, for example, a syringe. To flush the inner tube 16, a syringe may be connected to the hemostatic valve near the hub 14 of the delivery device 10, and then sterile liquid may be injected into the inner tube using the syringe.

In an alternate method of loading the valve 100 into the delivery device 10 and preparing same for use in a patient, the air bubbles may be removed from the distal sheath by submerging the distal sheath, the compression member 202, and the constricting member 300 in a container holding sterile liquid, such as saline. Additional sterile liquid may be injected into the delivery device 10 through the Y-connector 18 using a syringe, as discussed above. The distal sheath 30 of the delivery device 10 may then be shaken and gently tapped against a hard surface to remove air bubbles from the valve 100. The valve 100 may then pulled into the distal sheath 30, as discussed above.

In view of the tight fit between the collapsed valve 100 and the distal sheath 30, significant friction forces must be overcome in order to move the distal sheath 30 completely over the valve 100. To facilitate this procedure, the stent 102 may be substantially cooled, which, depending on the materials forming the stent, may enable the stent to more easily deform. Thus, once more than about one-half of the length of the stent 102 has been covered by the distal sheath 30, a cold liquid, such as saline solution, may be applied to the stent through the compression member 202 and the constricting member 300. This may be accomplished by removing the support member 204 from the compression member 202 and holding the remainder of the assembly in a substantially vertical orientation with the first end 208 of the funnel 206 facing upwardly. The cold liquid may then be introduced into the compression member 202 using any suitable apparatus. It will, of course, be appreciated that the cold liquid may thus serve two purposes—it may cool the stent 102, and it may serve as the deairing liquid in the deairing procedure described above.

Figure 20:
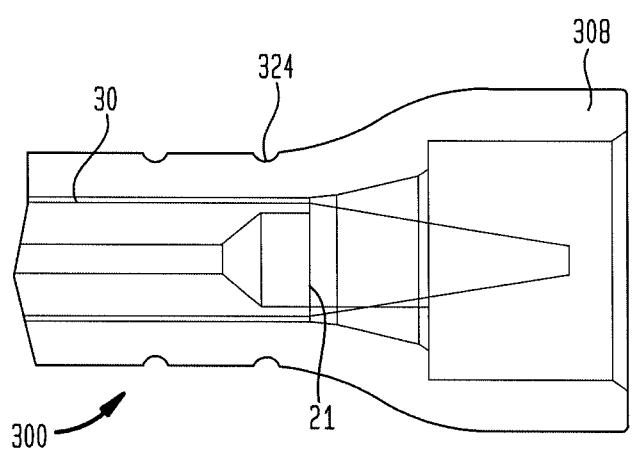

In order for the cooling of the stent 102 to be effective in making it easier for the stent to be completely covered by the distal sheath 30 of the delivery device 10, the stent should be cooled to a temperature below the transition temperature of the material forming the stent. The "transition temperature" of a material is the temperature at which the material changes from one crystal state to another. For the nitinol stents that may be employed in the present invention, a saline solution at about 0° C. may be used. When cooled below its transition temperature, the stent 102 becomes plastic, enabling it to deform much more readily under the forces exerted by the movement of the distal sheath 30 thereover. Accordingly, after the stent 102 has been cooled below the transition temperature, the user may completely cover the stent 102 with the distal sheath 30 of the delivery device 10, as illustrated in FIG. 20.

The distal sheath 30 of the delivery device 10 should be non-traumatic. To accomplish this, the distal sheath 30 may be made of soft polymeric material. However, while the valve 100 is loaded into the delivery device 10, the distal end 21 of the distal sheath 30 may slightly expand or flare due to the pressure exerted by the self-expanding stent 102. Since the distal sheath 30 is typically formed from a soft polymer, the distal end 21 of the distal sheath may not return to its original shape once the distal sheath completely covers the valve 100. It is nonetheless important to maintain the original cross-sectional profile of the distal end 21 of the distal sheath 30, because doing so makes the distal sheath more atraumatic and reduces the loading forces required to load the valve 100 into the delivery device 10. In order to maintain the original circular profile of the distal end 21 of the distal sheath 30, the loading assembly 200 preferably includes the constricting member 300 described above.

The present invention contemplates that the delivery device 10 and the loading assembly 200 may be provided together in the form of a kit. Thus, the kit may include a delivery device 10 for delivering the heart valve into the patient, as well as a loading assembly 200 for loading the heart valve into the delivery device. The loading assembly 200 would include all of the components necessary to load a heart valve into the delivery device, regardless of the size of heart valve to be deployed. In other words, the loading assembly 200 would include a compression member 202, a support member 204, and a constricting member 300, as well as a spacer 270. In cases in which the heart valve to be deployed is relatively large, the spacer would not be used to reduce the depth of the recess 226 in support member 204. However, where the heart valve to be deployed is relatively small, spacer 270 may be used to assure that the retainers 118 of the heart valve stent 102 protrude through the opening 218 of compression member 202, as shown in FIG. 14. It will be appreciated that, where there is a large range in heart valve sizes that may be deployed by delivery device 10, the kit may include multiple spacers 270, each spacer being sized for use with one or more heart valve sizes, the support surface or other surface of each spacer being marked with an indicia of the valve size that spacer is intended to be used with. Alternatively, the spacer could be color-coded for use with one or more heart valve sizes. In that regard, the thickness of annular portion 272 may differ from one spacer 270 to another so as to reduce the depth of recess 226 by an appropriate amount to accommodate the size of the particular heart valve being loaded into delivery device 10.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. An assembly for loading a self-expanding prosthetic heart valve into a delivery device, comprising:
    a compression member having a first open end with a first diameter, a second open end with a second diameter less than the first diameter, and a tapered wall decreasing in diameter from the first open end to the second open end, the tapered wall defining an open space adapted to receive the heart valve;
    a support member having a base on a first end and a recess on a second end, the recess having a fixed depth between a support surface of the recess and an open end of the recess, the recess being adapted to receive an end of the heart valve, the support member and the compression member being movable relative to one another between an initial position in which the base of the support member is relatively far from the first open end of the compression member and an operative position in which the base of the support member is relatively close to the first open end of the compression member, wherein movement of the support member and the compression member from the initial position to the operative position pushes the heart valve through the open space such that the heart valve is radially compressed by the tapered wall of the compression member as the heart valve advances through the open space;
    a constricting member having a first end and a second end, the second end of the constricting member being sized to receive the compressed heart valve from the second open end of the compression member; and
    a spacer adapted for assembly in the recess so that the recess has a depth between a support surface of the spacer and the open end of the recess which is less than the fixed depth.

2. The assembly according to claim 1, further comprising
a tubular extension on the second open end of the compression member, the tubular extension having a lumen therethrough; and
a first seal interposed between the delivery device and the tubular extension of the compression member.

3. The assembly according to claim 1, further comprising a tubular extension on the second open end of the compression member, the tubular extension having a lumen therethrough, the lumen having a diameter which is substantially equal to the second diameter.

4. The assembly according to claim 3, wherein the second end of the constricting member is sized and shaped for assembly to the tubular extension.

5. The assembly according to claim 1, further comprising a locking assembly for locking the compression member to the support member.

6. The assembly according to claim 5, wherein the locking assembly includes a male connecting member on one of the support member or the compression member, and a female connecting member on the other of the support member or the compression member for mating with the male connecting member.

7. The assembly according to claim 6, wherein the male connecting member includes a plurality of pins extending in radial directions from the longitudinal axis of the one of the support member or the compression member, and the female connecting member includes a plurality of features on the other of the support member or the compression member adapted to mate with the plurality of pins.

8. The assembly according to claim 1, wherein the support member has a through bore extending from the base to the recess, the through bore being sized to receive a tip of the delivery device therethrough.

9. The assembly according to claim 8, wherein the spacer is releasably connectable to the through bore.

10. A method for loading a self-expanding prosthetic heart valve into a delivery device, the delivery device including a tip, a retaining element, a compartment defined between the tip and the retaining element and adapted to receive the heart valve, and a distal sheath movable between a closed position fully covering the compartment and an open position uncovering the compartment, and the heart valve including a stent, a valve assembly supported by the stent, and at least one retainer at one end of the stent, the heart valve having an expanded condition and a collapsed condition, the method comprising:
configuring a support member to receive an end of the heart valve, the support member having a base on a first end and a recess on a second end, the recess having a fixed depth between a support surface of the recess and an open end of the recess, the configuring step including assembling a spacer in the recess so that the recess has a depth between a support surface of the spacer and the open end of the recess which is less than the fixed depth;
inserting the end of the heart valve in the expanded condition into the recess of the support member;
advancing the support member and a compression member toward one another, the compression member having an inner surface which decreases in diameter uniformly from a first open end to a second open end, the advancing step including advancing the heart valve through the compression member until the at least one retainer protrudes from the second open end of the compression member;
positioning the delivery device in an initial position in a constricting member, the constricting member having a first end, a second end, and an elongated tubular portion between the first end and the second end, the delivery device in the initial position having the distal sheath in the open position and the retaining element positioned outside the constricting member;
attaching the at least one retainer of the heart valve to the retaining element of the delivery device; and
moving the distal sheath of the delivery device to the closed position, during which the heart valve is advanced through the second open end of the compression member and into the elongated tubular portion of the constricting member to place the heart valve in the collapsed condition.

11. The method according to claim 10, further comprising filling at least a portion of the compression member with a sterile liquid before moving the distal sheath of the delivery device to the closed position to remove air from the heart valve and the delivery device.

12. The method according to claim 10, further comprising joining the constricting member to the compression member after attaching the at least one retainer of the heart valve to the retaining element of the delivery device.

13. The method according to claim 10, further comprising connecting the support member to the compression member after the advancing step.

14. A kit for delivering a self-expanding prosthetic heart valve to an implantation site in a patient, the heart valve being one of a plurality of different sizes, the kit comprising:
a delivery device including a tip, a retaining element, a compartment defined between the tip and the retaining element and adapted to receive the heart valve, and a distal sheath movable between a closed position fully covering the compartment and an open position uncovering the compartment;
a compression member having a first open end with a first diameter, a second open end with a second diameter less than the first diameter, and a tapered wall decreasing in diameter from the first open end to the second open end, the tapered wall defining an open space adapted to receive the heart valve;
a support member having a base on a first end and a recess on a second end, the recess having a fixed depth between a support surface of the recess and an open end of the recess, the recess being adapted to receive an end of the heart valve, the support member and the compression member being movable relative to one another between an initial position in which the base of the support member is relatively far from the first open end of the compression member and an operative position in which the base of the support member is relatively close to the first open end of the compression member, wherein movement of the support member and the compression member from the initial position to the operative position pushes the heart valve through the open space such that the heart valve is radially compressed by the tapered wall of the compression member as the heart valve advances through the open space;
a constricting member having a first end and a second end, the second end of the constricting member being sized to receive the compressed heart valve from the second open end of the compression member; and
a spacer adapted for assembly in the recess so that the recess has a second depth between a support surface of the spacer and the open end of the recess which is less than the fixed depth,
wherein the fixed depth of the recess is adapted for use with a heart valve having a first compressed length, and the second depth of the recess is adapted for use with a heart valve having a compressed length less than the first compressed length.

15. The kit according to claim 14, further comprising a plurality of spacers adapted for assembly in the recess, each spacer being adapted to reduce the depth of the recess by a selected amount, the selected amount for one spacer being different from the selected amount for each of the other spacers.

* * * * *